(12) United States Patent
Muderlak et al.

(10) Patent No.: US 8,931,713 B2
(45) Date of Patent: Jan. 13, 2015

(54) DISPENSING SYSTEM FOR ODOR CONTROL

(75) Inventors: Ken Muderlak, Milwaukee, WI (US); Todd Muderlak, Whitefish Bay, WI (US)

(73) Assignee: Dispensing Dynamics International, City of Industry, CA (US)

( * ) Notice: Subject to any disclaimer, the term of this patent is extended or adjusted under 35 U.S.C. 154(b) by 639 days.

(21) Appl. No.: 13/373,062

(22) Filed: Nov. 3, 2011

(65) Prior Publication Data

US 2013/0032641 A1    Feb. 7, 2013

Related U.S. Application Data

(60) Provisional application No. 61/411,836, filed on Nov. 9, 2010.

(51) Int. Cl.
*A24F 25/00*   (2006.01)
*A61L 9/04*    (2006.01)
*A61L 9/12*    (2006.01)

(52) U.S. Cl.
CPC ............. *A61L 9/12* (2013.01); *A61L 2209/133* (2013.01); *A61L 2209/15* (2013.01)

USPC ................................. 239/60; 239/37; 239/58

(58) Field of Classification Search
CPC .................................. A24F 25/00; A61L 9/04
USPC .............................. 239/34, 35, 57, 58, 59, 60
See application file for complete search history.

(56) References Cited

U.S. PATENT DOCUMENTS

| 4,166,087 | A | * | 8/1979 | Cline et al. | 261/96 |
| 4,383,951 | A | * | 5/1983 | Palson | 261/30 |
| 4,931,258 | A | * | 6/1990 | Zlotnik et al. | 422/124 |
| 5,673,825 | A | * | 10/1997 | Chen | 222/646 |
| 6,039,212 | A | * | 3/2000 | Singh | 222/30 |
| 2005/0002834 | A1 | * | 1/2005 | Gohil | 422/123 |
| 2007/0235555 | A1 | * | 10/2007 | Helf et al. | 239/102.2 |

* cited by examiner

*Primary Examiner* — Justin Jonaitis
(74) *Attorney, Agent, or Firm* — Thomas R. Lampe

(57) ABSTRACT

Apparatus for dispensing fragrance from a refill component that is installed and removed along a vertical axis through an opening at the bottom of the housing of the apparatus includes securing structure for releasably securing the refill component to the housing when the refill component is in the housing interior in operative position.

18 Claims, 4 Drawing Sheets

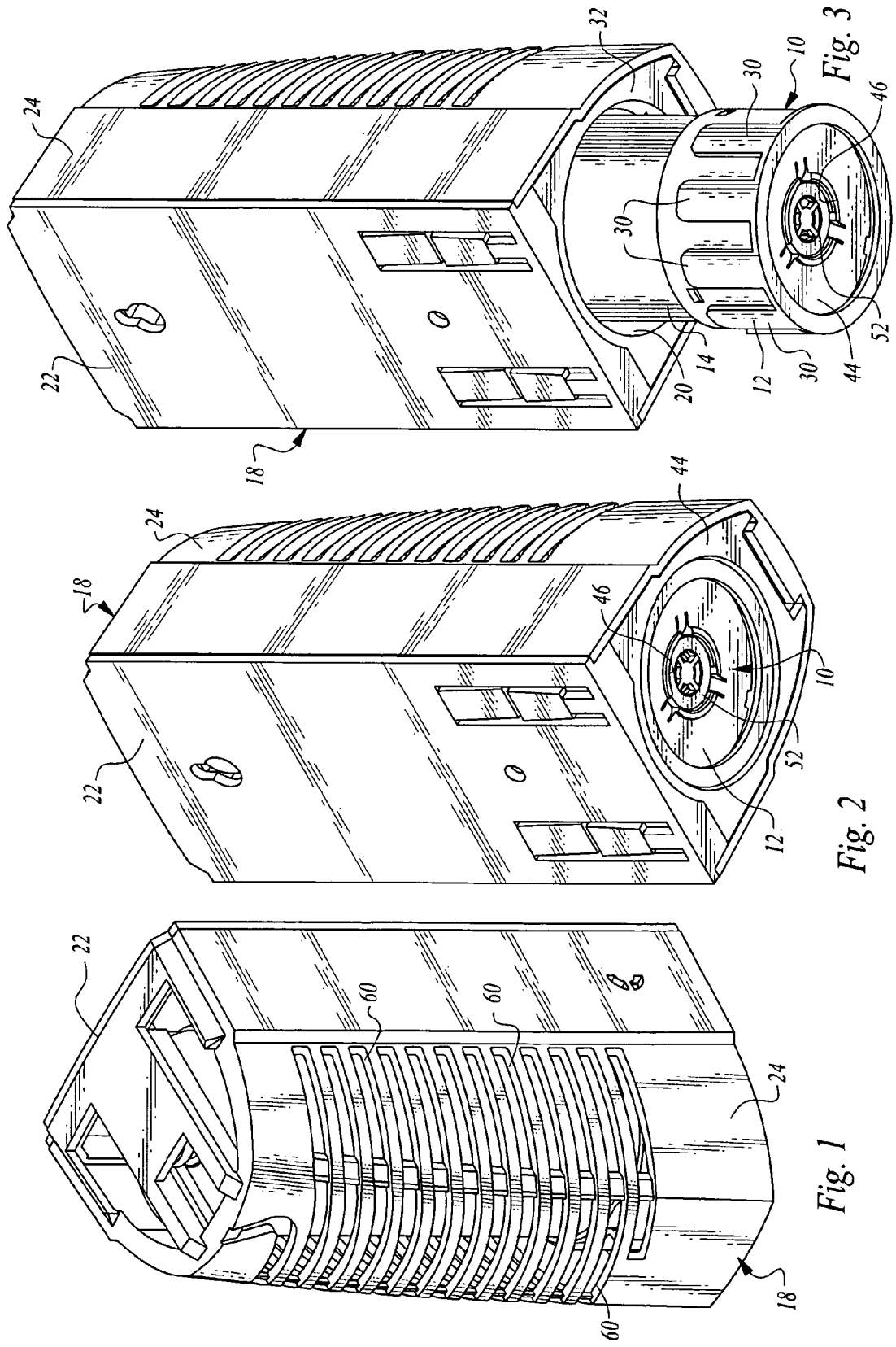

US 8,931,713 B2

DISPENSING SYSTEM FOR ODOR CONTROL

This Application is based on and claims the benefit of the filing date of U.S. Provisional Patent Application No. 61/411,836, filed Nov. 9, 2010.

TECHNICAL FIELD

The present invention relates to apparatus for dispensing fragrances associated with substances for odor control. An odor control refill component having an odor control substance is inserted in and removed from a housing of the apparatus along a substantially vertical axis from below. The odor control substance is emitted from the housing of the apparatus.

BACKGROUND OF THE INVENTION

Numerous devices and approaches are known for dispensing fragrances for odor control purposes. The fragrances are dispensed from air control substances of varying types and forms, including gels, absorbent wicks, gases, liquids, and solids. It is known to incorporate these odor control substances in refill containers which are utilized with dispenser housings or supports. Some prior art dispensers are electrically powered, employing fans and/or heating elements to promote fragrance dispensing.

DISCLOSURE OF INVENTION

The apparatus of the present invention is also for dispensing the fragrance of an odor control substance from a refill component having a quantity of the substance.

The apparatus allows for insertion and removal of a container from the bottom and along a substantially vertical axis. The amount of time and effort to place or remove a refill component can be decreased compared to a dispensing system which requires the removal of a system cover or rotating the cover on a hinge to access a refill component for replacement or other purposes. This added convenience can be significant.

Also, the refill component of this invention can include features which allow for mechanical or electronic lock outs so that only a predetermined refill component can work in a corresponding dispensing system. Further, the refill component can be secured into the dispensing system if required and released by a key or a finger. The dispensing system can be either a passive system or an active system. Additionally, certain settings relating to the insertion of a fresh refill component can be reset or initiated by use of a sensor, such as a micro-switch, to detect the insertion.

The application discloses two embodiments, one of which is a passive system, that is, one that relies on a structure, such as an absorbent wick, to naturally (through capillary or other action) introduce the fragrance/odor control substance into the surrounding environment. A second embodiment is an active system employing an additional module including a power source and fan to act as air movement agent to draw the fragrance/odor control substance from the system and into the surrounding environment.

The apparatus for dispensing the fragrance of an odor control substance includes a refill component having a quantity of odor control substance. The apparatus further includes a housing defining a housing interior for receiving the refill component and further defining a housing opening at the bottom of the housing communicating with the housing interior and allowing for the passage of the refill component through the housing opening along a substantially vertical axis between a first position wherein said refill component is located in said housing interior and a second position wherein said refill component is located below said housing, whereby the refill component is selectively alternatively movable substantially vertically upwardly through the housing opening to enable dispensing of the fragrance of the substance by the apparatus or movable vertically downwardly through the housing opening to remove the refill component from the housing.

Securing structure is provided for releasably securing the refill component to the housing in said first position.

Other features, advantages and objects of the present invention will become apparent with reference to the following description and accompanying drawings.

BRIEF DESCRIPTION OF DRAWINGS

FIG. 1 is a front perspective view of apparatus constructed in accordance with the teachings of the present invention;

FIG. 2 is a bottom, rear perspective view of the apparatus showing the refill component in operative position relative to the housing;

FIG. 3 is a view similar to FIG. 3 partially removed from the housing;

BEST MODE FOR CARRYING OUT THE INVENTION

Figure 4:
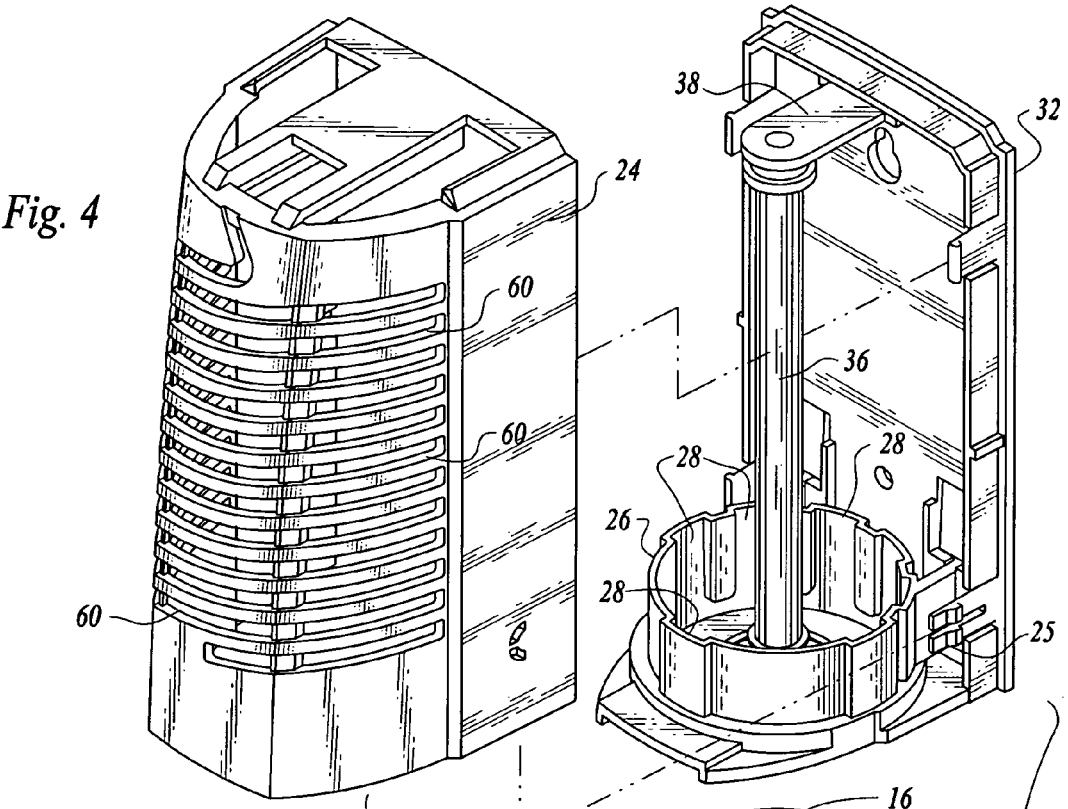
FIG. 4 is an exploded, perspective view illustrating the housing cover, a housing back portion and refill component separated from one another.

Referring now to the drawings, apparatus constructed in accordance with the teachings of the present invention includes a refill component 10 having a quantity of odor control substance. In the arrangement illustrated, the refill component includes a cup-shaped container 12 and a quantity of odor control substance supported by the container and projecting outwardly from the interior thereof. In this particular instance the odor control substance is in a saturated wick 14 having a tubular configuration and defining a central hole 16 extending the length thereof. It will of course be appreciated that the principles of the present invention can be applied to other types of odor control substance delivery systems.

Figure 6:
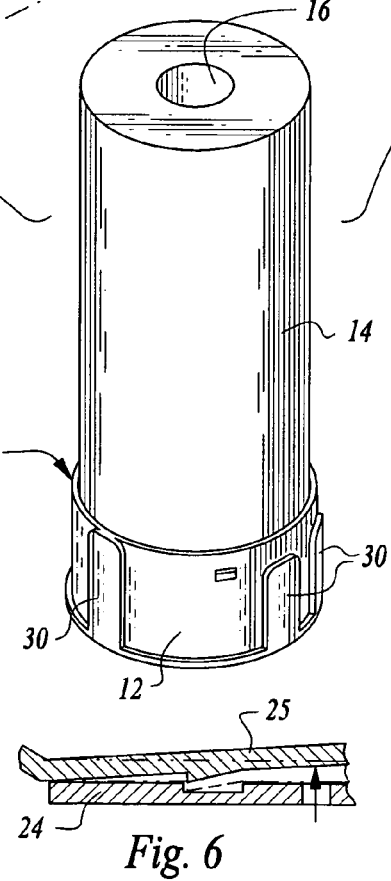
FIG. 6 is an enlarged, cross-sectional view showing portions of latch mechanism employed between the cover and housing back portion.

The dispensing system additionally includes a housing 18 defining a housing interior for receiving the refill component and further defining a housing opening 20 at the bottom of the housing communicating with the housing interior. The housing includes a housing back portion 22 and a cover 24 moveable relative to the housing back portion to open or close the housing. A suitable latch such as flexible live hinge latch member 25 may be used to latch the cover in closed position. FIG. 6 shows the latch member being moved to unlatched position by exerting a force thereon through a keyhole in the cover.

As will be described in detail below, the refill component 10 may be passed through the housing opening along a substantially vertical axis between a first position wherein the refill component is located in the housing interior and a second position wherein the refill component is located below the housing, whereby the refill component is selectively alternatively moveable substantially vertically upwardly through the housing opening to enable dispensing of the fragrance of the substance by the apparatus or moveable vertically downwardly through the housing opening to remove the refill component from the housing.

Surrounding the housing opening 20 and projecting upwardly from the housing bottom is a generally cylindrically-shaped wall 26. Wall 26 defines a plurality of female elements in the form of recesses 28 extending vertically. Container 12 of the refill component 10 has a plurality of vertically extending spaced male members or elements 30. The female elements or recesses 28 of the cylindrically-shaped wall 26 must match up with the male elements 30; otherwise the container 12 will be precluded from entering the confines of the cylindrically-shaped wall 26. That is, the refill component and the housing must have a predetermined compatible character to enable the refill component to move to operating position within the housing. Such an arrangement can be utilized as a lock out feature to ensure that the housing is being refilled by an appropriate refill component. The housing bottom 32 can provide the refill compliancy, lock out functionality, and act to prevent a user from touching the odor control substance on the wick 14. The saturated wick can for example be impregnated plastic and utilize capillary action to provide the fragrance/odor control substance to the environment.

The apparatus includes securing structure for releasably securing the refill component to the housing when the refill component is disposed within the housing in operative or first position. More particularly, the securement structure comprises a support member attached to the housing, extending downwardly within the interior of the housing and releasably secured to the refill component when the refill component is in operative position.

Figure 7:
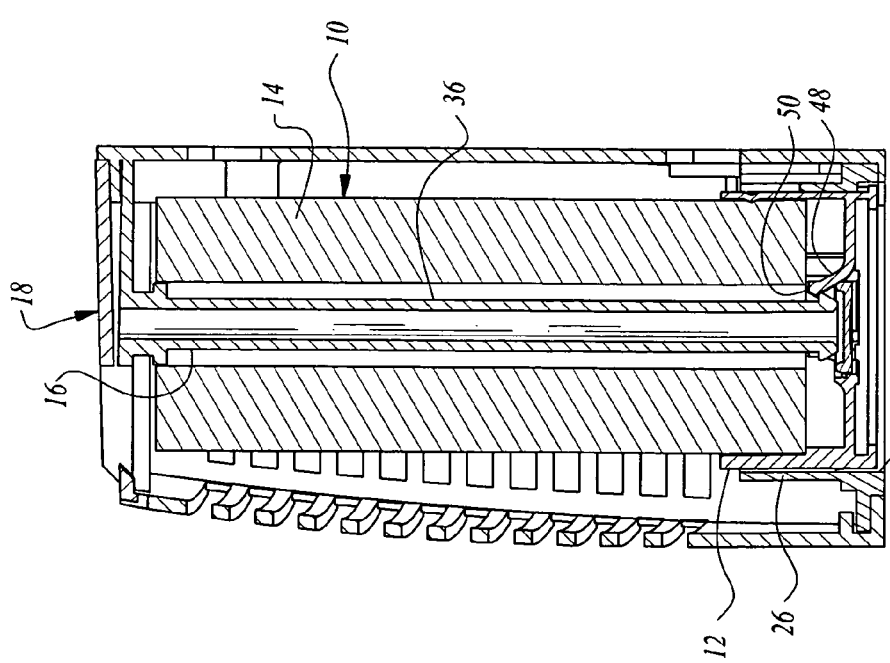
FIG. 7 is a side elevational, cross-sectional view showing the refill component, including container and wick, in operative position within the housing.

The support member comprises a rod or shaft 36 extending downwardly from the top of the housing back, a projecting support 38 positioning the rod 36 coaxially with the center of cylindrical wall 26. The rod 36 has a rod distal end having an enlargement 40. When the refill component is inserted into the interior of the housing, the rod 36 extends through elongated opening 16 of the wick. This is shown, for example, in FIGS. 5 and 7.

Lock structure is employed to releasably lock the container of the refill component to the rod. This will be described in detail below.

The bottom wall 44 of container 12 has a circular-shaped opening 46 located at the center thereof. A plurality of lock members in the form of flexible living hinge locks 48 having distal ends 50 which extend inwardly over circular-shaped opening 46 normally project over circular-shaped opening 46.

Figure 5:
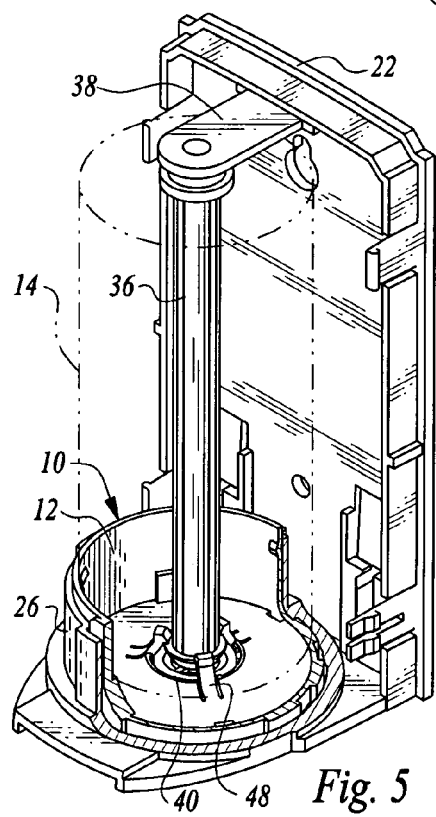
FIG. 5 is a perspective view in partial cross-section illustrating the container of the refill component in operative position on the back portion of the housing, a wick supported by the container shown by broken lines.

When the refill component 10 is manually pushed upwardly to insert the refill component within the housing, the distal ends 50 will snap over enlargement 40 at the distal end of the rod and connect the rod and refill component together. FIGS. 5 and 6 illustrate this condition.

Unlocking structure in the form of disc-like element 52 is rotatably mounted at the bottom of the container at the location of circular-shaped opening 46. The element 52 is normally slightly spaced from and below the distal end of the rod 36 when the refill component is in operative position within the housing. When, however, it is necessary or desirable to remove the refill component from the housing, this action may be accomplished by rotating the disc-like element 52, for example by finger or through use of a key.

Figure 8:
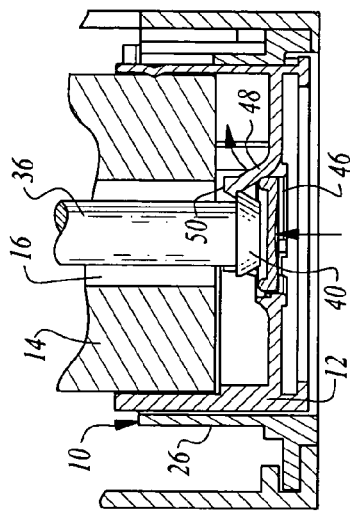
FIGS. 8-10 are cross-sectional views of components of the apparatus in the relative positions assumed thereby during consecutive stages of unlocking the refill component from the housing and a support rod in the housing interior.
Figure 9:
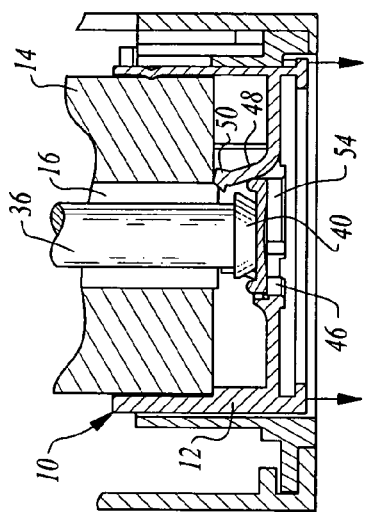
Figure 10:
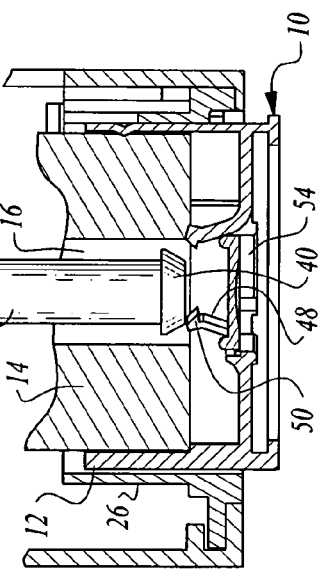

The bottom wall 44 of container 12 forms a ramp 54 engaging the disc-like element 52 which will cause upward movement of the disc-like element 52 relative to the bottom upon rotation thereof. FIGS. 8-10 provide an illustration of how the disc-like element serves to unlock the refill component from the housing. In FIG. 8, initial contact between the disc-like element's upper edge and the flexible living hinge locks 48 will serve to displace the distal ends 50 of the hinge locks outwardly as shown by the arrow in FIG. 8. Further upward movement of the disc-like element responsive to further rotation thereof and engagement with the ramp will bend the flexible living hinge locks outwardly far enough to completely withdraw from contact with the enlarged distal end of the rod. The refill component is then unsupported by the rod and is free to drop in the direction of the arrows shown in FIG. 9. FIG. 10 shows the refill component having moved downwardly and the distal ends of the flexible living hinge locks disposed below the rod distal end. The container 12 of the unsupported removed refill component can then be readily grasped to complete extraction and removal of the refill component so that it may be replaced by another.

In the configuration described above, the apparatus is essentially a passive system that relies on an element, such as an absorbent wick, to naturally (through capillary or other action) send the fragrance of the odor control substance into the environment through air openings 60 defined by the cover 24 of the housing. If desired, the apparatus can be converted from a passive system to an active system to create air flow into, through and out of the housing, that is, to draw the fragrance from the odor control substance of the refill component and cause dissemination of the fragrance through the air openings into the surrounding environment.

Figure 13:
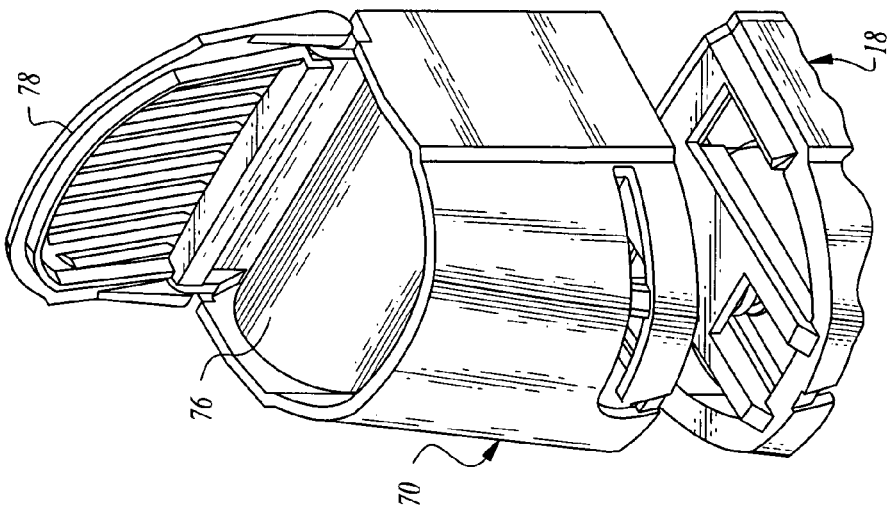
FIG. 13 is a perspective view illustrating the fan module separated from the housing.
Figure 12:
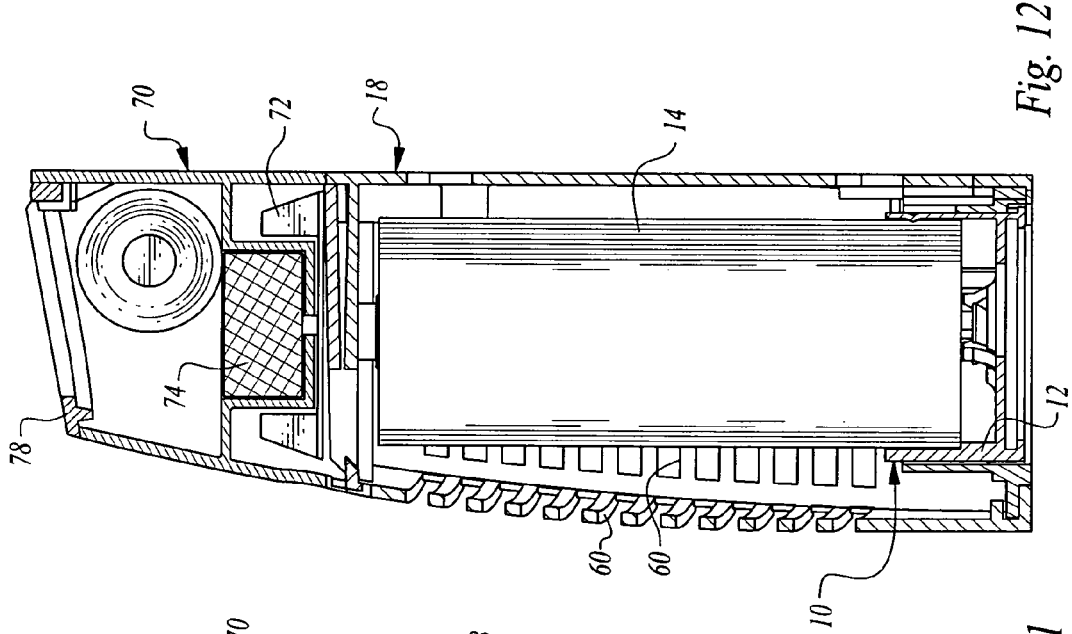
FIG. 12 is a side, cross-sectional view of the arrangement of FIG. 11.
Figure 11:
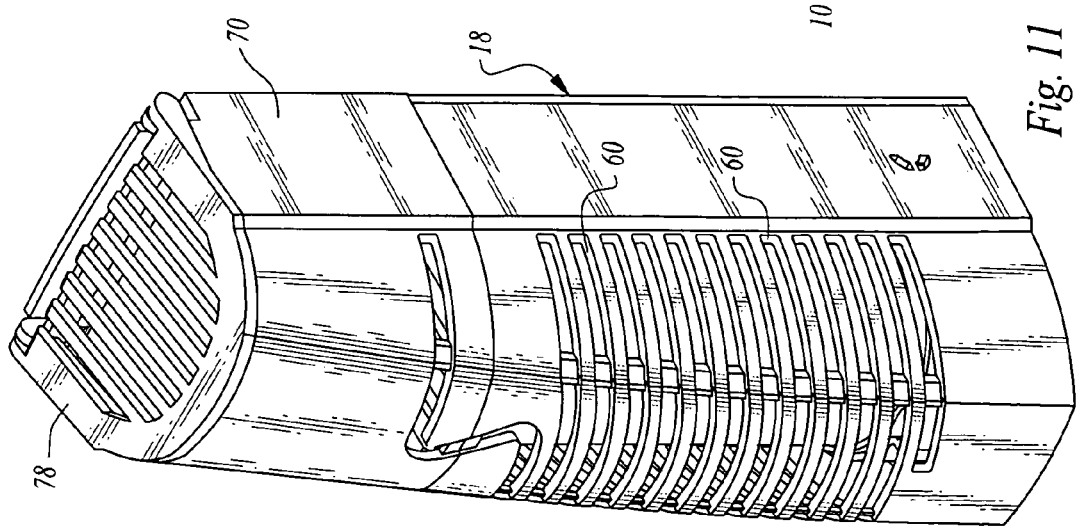
FIG. 11 is a perspective view of the dispensing apparatus with a fan module attached thereto.

FIGS. 11-13 disclose a fan module 70 which may be attached to the upper end of the housing 18 and utilized to convert the system from a passive system to an active system. FIG. 13 shows the fan module 70 prior to placement on the housing 18 and suitable interconnection structure on the housing 18 and the fan module 18 is utilized to releasably attach the fan module in place. It is to be noted that the upper end of the housing 18 has openings formed therein. The fan module also has openings at the bottom thereof to provide air flow communication between a fan 72 in the module and the housing interior. In the arrangement shown, the fan is driven by an electric motor 74, a battery 76 in a battery compartment being the energy source. Any of various types of fans can be utilized to help disperse the fragrance of the refill component and cause exit thereof through air openings 60. A lid 78 allows access to the hinged battery. Other types of energy sources could be employed; for example, light harvesting devices.

An air opening 80 formed in the outer wall of the fan module allows fan induced air to flow into the fan module interior, and thence into the interior of housing 18 so that fragrance is entrained before exiting openings 60.

The invention claimed is:

1. Apparatus for dispensing the fragrance of an odor control substance, said apparatus comprising, in combination:
a refill component having a quantity of said odor control substance;
a housing defining a housing interior for receiving said refill component and further defining a housing opening at the bottom of said housing communicating with said housing interior and allowing for the passage of said refill component through said housing opening along a substantially vertical axis between a first position wherein said refill component is located in said housing interior and a second position wherein said refill component is located below said housing, whereby the refill component is selectively movable between said first and second positions, said refill component when moving from said second position to said first position moving substantially vertically upwardly through the housing opening to enable dispensing of the fragrance of said substance by said apparatus and said refill component when moving from said first position to said second position moving substantially vertically downwardly through the housing opening to remove the refill component from the housing; and
securing structure for releasably securing said refill component to said housing in said first position, said securing structure comprising a support member attached to said housing, extending downwardly within the interior of said housing and releasably secured to said refill component when said refill component is in said first position, said refill component including a container defining an interior holding said substance, said support member releasably secured to said container when said refill component is in said first position, said container including lock structure for releasably locking said support member to said container, said lock structure including at least one lock member connected to the remainder of said container and frictionally engageable with said support member, and said support member comprising a rod having a rod distal end positioned adjacent to said at least one lock member and lockingly engageable thereby when said refill component is in said first position, said rod having an enlargement at said rod distal end lockingly engageable by said at least one lock member.

2. The apparatus according to claim 1 wherein said housing includes a housing back portion and a cover movable relative to said housing back portion to open or close said housing.

3. The apparatus according to claim 1 wherein said housing defines a plurality of air openings for allowing the passage of air out of said housing interior.

4. The apparatus according to claim 1 wherein said securing structure comprises structural features on said refill component and on said housing of predetermined compatible character enabling placement of said refill component in said housing interior and releasable securement of said refill component to said housing.

5. The apparatus according to claim 4 wherein said structural features include at least one male element on the refill, component and at least one corresponding female element on the cover.

6. The apparatus according to claim 1 additionally comprising a fan module including a fan attached to said housing for drawing air into said housing interior and past said substance when said refill component is in said first position to entrain said fragrance and dispense said fragrance from said housing.

7. The apparatus according to claim 1 wherein said container includes ramp structure and wherein said unlocking structure is rotatably mounted for engagement with said ramp structure, said ramp structure causing upward movement of said unlocking structure during rotation thereof.

8. The apparatus according to claim 1 wherein said refill component and said housing are of predetermined compatible character enabling said refill component to move to said first position.

9. Apparatus for dispensing the fragrance of an odor control substance from a refill component having a quantity of said odor control substance, said apparatus comprising, in combination:
a housing defining a housing interior for receiving said refill component and further defining a housing opening at the bottom of said housing communicating with said housing interior and allowing for the passage of said refill component through said housing opening along a substantially vertical axis between a first position wherein said refill component is located in said housing interior and a second position wherein said refill component is located below said housing, whereby the refill component is selectively movable between said first and second positions, said refill component when moving from said second position to said first position moving substantially vertically upwardly through the housing opening to enable dispensing of the fragrance of said substance by said apparatus and said refill component when moving from said first position to said second position moving substantially vertically downwardly through the housing opening to remove the refill component from the housing; and
securing structure for releasably securing said refill component to said housing in said first position, said securing structure comprising a support member attached to said housing, extending downwardly within the interior of said housing and releasably secured to said refill component when said refill component is in said first position, said refill component including a container defining an interior holding said substance, said support member releasably secured to said container when said refill component is in said first position, said container including lock structure for releasably locking said support member to said container, said lock structure including at least one lock member connected to the remainder of said container and frictionally engageable with said support member, said support comprises a rod having a rod distal end positioned adjacent to said at least one lock member and lockingly engageable thereby when said refill component is in said first position, said container additionally including unlocking structure selectively moveable relative to said at least one lock member to remove said at least one lock member from locking engagement with said rod distal end enabling said refill component to move from said first position to said second position.

10. The apparatus according to claim 9 wherein said securing structure comprises structural features on said refill component and on said housing of predetermined compatible character enabling placement of said refill component in said housing interior and releasable securement of said refill component to said housing.

11. The apparatus according to claim 9 wherein a plurality of spaced lock members are connected to the remainder of said container, said unlocking structure selectively moveable relative thereto to remove all of said lock members from locking engagement with said rod distal end.

12. The apparatus according to claim 9 wherein said unlocking structure is rotatably mounted at the bottom of said container, rotation of said unlocking structure causing movement of said unlocking structure upwardly in the direction of said rod distal end relative to said bottom and displacement of said at least one lock member away from said rod distal end.

13. The apparatus according to claim 12 wherein said container includes ramp structure and wherein said unlocking structure is rotatably mounted for engagement with said ramp structure, said ramp structure causing upward movement of said unlocking structure during rotation thereof.

14. Apparatus for dispensing the fragrance of an odor control substance, said apparatus comprising, in combination:
   a refill component having a quantity of said odor control substance;
   a housing defining a housing interior for receiving said refill component and further defining a housing opening at the bottom of said housing communicating with said housing interior and allowing for the passage of said refill component through said housing opening along a substantially vertical axis between a first position wherein said refill component is located in said housing interior and a second position wherein said refill component is located below said housing, whereby the refill component is selectively movable between said first and second positions, said refill component when moving from said second position to said first position moving substantially vertically upwardly through the housing opening to enable dispensing of the fragrance of said substance by said apparatus and said refill component when moving from said first position to said second position moving substantially vertically downwardly through the housing opening to remove the refill component from the housing; and
   securing structure for releasably securing said refill component to said housing in said first position, said securing structure comprising a support member attached to said housing, extending downwardly within the interior of said housing and releasably secured to said refill component when said refill component is in said first position, said refill component including a container defining an interior holding said substance, said support member releasably secured to said container when said refill component is in said first position, said container including lock structure for releasably locking said support member to said container, said lock structure including at least one lock member connected to the remainder of said container and frictionally engageable with said support member, and said support member comprising a rod having a rod distal end positioned adjacent to said at least one lock member and lockingly engageable thereby when said refill component is in said first position, said container including unlocking structure selectively moveable relative to said at least one lock member to remove said at least one lock member from locking engagement with said rod distal end enabling said refill component to move from said first position to said second position.

15. The apparatus according to claim 14 wherein a plurality of spaced lock members are connected to the remainder of said container, said unlocking structure selectively moveable relative thereto to remove all of said lock members from locking engagement with said rod distal end.

16. The apparatus according to claim 15 wherein said spaced lock members comprise living hinge locks.

17. The apparatus according to claim 14 wherein said unlocking structure is rotatably mounted at the bottom of said container, rotation of said unlocking structure causing movement of said unlocking structure upwardly in the direction of said rod distal end relative to said bottom and displacement of said at least one lock member away from said rod distal end.

18. Apparatus for dispensing the fragrance of an odor control substance, said apparatus comprising, in combination:
   a refill component having a quantity of said odor control substance;
   a housing defining a housing interior for receiving said refill component and further defining a housing opening at the bottom of said housing communicating with said housing interior and allowing for the passage of said refill component through said housing opening along a substantially vertical axis between a first position wherein said refill component is located in said housing interior and a second position wherein said refill component is located below said housing, whereby the refill component is selectively movable between said first and second positions, said refill component when moving from said second position to said first position moving substantially vertically upwardly through the housing opening to enable dispensing of the fragrance of said substance by said apparatus and said refill component when moving from said first position to said second position moving substantially vertically downwardly through the housing opening to remove the refill component from the housing; and
   securing structure for releasably securing said refill component to said housing in said first position, said securing structure comprising a support member attached to said housing, extending downwardly within the interior of said housing and releasably secured to said refill component when said refill component is in said first position, said support member extending through said odor control substance.

* * * * *